United States Patent
Lenne et al.

(10) Patent No.: US 8,465,920 B2
(45) Date of Patent: Jun. 18, 2013

(54) METHOD FOR HYBRIDIZING NUCLEIC ACIDS

(75) Inventors: Nathalie Lenne, Muttersholtz (FR); Patrick Erbacher, Benfeld (FR)

(73) Assignees: Polyplus Transfection SA, Illkirch Cedex (FR); Centre National de la Recherche Scientifique, Paris Cedex (FR); Universite de Strasbourg, Strasbourg (FR)

( * ) Notice: Subject to any disclaimer, the term of this patent is extended or adjusted under 35 U.S.C. 154(b) by 296 days.

(21) Appl. No.: 12/735,261

(22) PCT Filed: Sep. 12, 2008

(86) PCT No.: PCT/IB2008/002789
§ 371 (c)(1), (2), (4) Date: Jun. 25, 2010

(87) PCT Pub. No.: WO2009/083763
PCT Pub. Date: Jul. 9, 2009

(65) Prior Publication Data
US 2010/0311056 A1    Dec. 9, 2010

Related U.S. Application Data

(60) Provisional application No. 61/009,145, filed on Dec. 27, 2007.

(30) Foreign Application Priority Data

Dec. 27, 2007  (EP) .................................. 07025148

(51) Int. Cl.
*C12Q 1/68* (2006.01)
*C12P 19/34* (2006.01)

(52) U.S. Cl.
USPC ........................ 435/6.1; 435/91.1; 435/91.2

(58) Field of Classification Search
USPC ........................................ 435/6.1, 91.1, 91.2
See application file for complete search history.

(56) References Cited

U.S. PATENT DOCUMENTS
2003/0100113 A1 *   5/2003   Behr et al. .................... 435/455

FOREIGN PATENT DOCUMENTS
WO   WO 2006/052854   5/2006
WO   WO 2007/069092   6/2007

OTHER PUBLICATIONS

International Search Report for PCT/IB2008/054832, mailed Apr. 9, 2009.

(Continued)

*Primary Examiner* — Jezia Riley
(74) *Attorney, Agent, or Firm* — Nixon & Vaderhye P.C.

(57) ABSTRACT

The invention relates to a method for manipulating, isolating, detecting or amplifying a target nucleic acid in a sample by hybridization with an oligonucleotide-oligocation conjugate, comprising allowing said nucleic acid to react with an oligonucleotide-oligocation conjugate comprising at least A1 and Bj linked together directly or via a linker, wherein. A, is an i-mer oligonucleotides, with i=3 to 50, where Ai is an oligomer with naturally or non naturally occurring nucleobases and/or pentafuranosyl groups and/or native phosphodiester bonds, optionally comprising a marker group. Bj is a j-mer organic oligocation moiety, with j=1 to 50, where B is $-HPO_3-R_1-(NH-R_2)_n-NH-R_3-O-$, where $R_1$, $R_2$ and $R_3$ are lower alkylene, identical or different, $NH-R2$ moieties being identical or different when n is >1; $HPO_3-R_1-CH(X)-R_3-O-$, where Ri and R3, identical or different, are lower alkylene and X is putrescine, spermidine or spermine residue.

12 Claims, 9 Drawing Sheets

OTHER PUBLICATIONS

Figure 1:
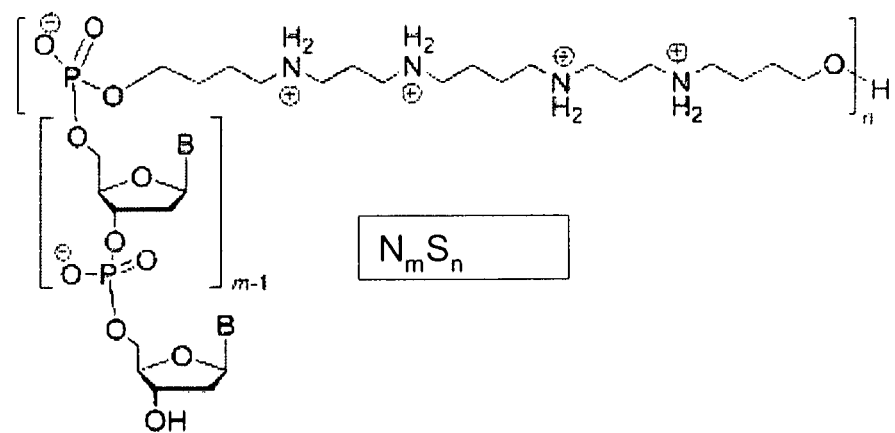

Pons Benedicte et al., "Online synthesis of di-block cationic oligonucleotides for enhanced hybridization to their complementary sequence", Chembiochem, vol. 7, No. 8, (Jan. 1, 2006), pp. 1173-1176.

Noir, R. et al., "Oligonucleotide-oligospermine conjugates (zip nucleic acids): A convenient means of finely tuning hybridization temperatures", Journal of the American Chemical Society, vol. 130, No. 40, (Sep. 10, 2008), pp. 13500-13505.

Noir et al., "Supplementary data", JACS, vol. 106, (Sep. 10, 2008), pp. 1-7.

Potier, P. et al., "Synthesis and hybridization properties of oligonucleotides containing polyamines at the C-2 position of pruines: a pre-synthetic approach for the incorporation of spermine into oligodeoxynucleotides containing 2-(4,9,13-triazatridecyl)-2'-deoxyguanosine", Chemistry—A European Journal, vol. 6, No. 22, (Nov. 17, 2000), pp. 4188-4194.

Ching-Hsuan, T. et al., "Polyamine-Linked Oligonucleotides for DNA Triple Helix Formation", Nucleic Acids Research, vol. 21, No. 23, (Jan. 1, 1993), pp. 5489-5494.

Sund, C. et al. "Synthesis of C-branched spermine tethered oligo-DNA and the thermal stability of the duplexes and triplexes", tetrahedron, vol. 52, No. 37, (Jan. 1, 1996), pp. 12275-12290.

Voirin, E. et al., "Versatile synthesis of oligodeoxyribonucleotide—Oligospermine conjugates", Nature Protocols, vol. 2, No. 6, (Jan. 1, 2007), pp. 1360-1367.

Schmid et al, "Recognition of DNA Sequences by Strand Replacement with Polyamino-oligonucleotides", Tetrahedron Letters, vol. 36, No. 9, pp. 1447-1450, 1995.

* cited by examiner a.

b.

c.

a.

b.

a.

b.

a.

| Probe | Raw background fluorescence |
|---|---|
| F-N22S4 | 4.8 |
| F-N22 | 24 | b.

c.

d.

a.

b.

SEQUENCE LISTING

<160> NUMBER OF SEQ ID NOS: 19

<210> SEQ ID NO 1
<211> LENGTH: 24
<212> TYPE: DNA
<213> ORGANISM: Artificial sequences
<220> FEATURE:
<223> OTHER INFORMATION: Oligonucleotides

<400> SEQUENCE: 1
gaggaggagg atgaaataga tggt                                         24

<210> SEQ ID NO 2
<211> LENGTH: 21
<212> TYPE: DNA
<213> ORGANISM: Artificial sequences
<220> FEATURE:
<223> OTHER INFORMATION: Oligonucleotides

<400> SEQUENCE: 2
gcccattaac aggtcttcca a                                            21

<210> SEQ ID NO 3
<211> LENGTH: 24
<212> TYPE: DNA
<213> ORGANISM: Artificial sequences
<220> FEATURE:
<223> OTHER INFORMATION: Oligonucleotides

<400> SEQUENCE: 3
gaggaggagg atgaaataga tggt                                         24

<210> SEQ ID NO 4
<211> LENGTH: 21
<212> TYPE: DNA
<213> ORGANISM: Artificial sequences
<220> FEATURE:
<223> OTHER INFORMATION: Oligonucleotides

<400> SEQUENCE: 4
gcccattaac aggtcttcca a                                            21

<210> SEQ ID NO 5
<211> LENGTH: 24
<212> TYPE: DNA
<213> ORGANISM: Artificial sequences
<220> FEATURE:
<223> OTHER INFORMATION: Oligonucleotides

<400> SEQUENCE: 5
gaggaggagg atgaaataga tggt                                         24

<210> SEQ ID NO 6
<211> LENGTH: 21
<212> TYPE: DNA
<213> ORGANISM: Artificial sequences
<220> FEATURE:
<223> OTHER INFORMATION: Oligonucleotides

<400> SEQUENCE: 6
gcccattaac aggtcttcca a                                            21

<210> SEQ ID NO 7
<211> LENGTH: 23
<212> TYPE: DNA

```
<213> ORGANISM: Artificial sequences
<220> FEATURE:
<223> OTHER INFORMATION: Oligonucleotides

<400> SEQUENCE: 7
tttgttactg ttgttgatac tac                                      23

<210> SEQ ID NO 8
<211> LENGTH: 25
<212> TYPE: DNA
<213> ORGANISM: Artificial sequences
<220> FEATURE:
<223> OTHER INFORMATION: Oligonucleotides

<400> SEQUENCE: 8
gaaaaataaa ctgtaaatca tattc                                    25

<210> SEQ ID NO 9
<211> LENGTH: 23
<212> TYPE: DNA
<213> ORGANISM: Artificial sequences
<220> FEATURE:
<223> OTHER INFORMATION: Oligonucleotides

<400> SEQUENCE: 9
tttgttactg ttgttgatac tac                                      23

<210> SEQ ID NO 10
<211> LENGTH: 25
<212> TYPE: DNA
<213> ORGANISM: Artificial sequences
<220> FEATURE:
<223> OTHER INFORMATION: Oligonucleotides

<400> SEQUENCE: 10
gaaaaataaa ctgtaaatca tattc                                    25

<210> SEQ ID NO 11
<211> LENGTH: 23
<212> TYPE: DNA
<213> ORGANISM: Artificial sequences
<220> FEATURE:
<223> OTHER INFORMATION: Oligonucleotides

<400> SEQUENCE: 11
tttgttactg ttgttgatac tac                                      23

<210> SEQ ID NO 12
<211> LENGTH: 25
<212> TYPE: DNA
<213> ORGANISM: Artificial sequences
<220> FEATURE:
<223> OTHER INFORMATION: Oligonucleotides

<400> SEQUENCE: 12
gaaaaataaa ctgtaaatca tattc                                    25

<210> SEQ ID NO 13
<211> LENGTH: 24
<212> TYPE: DNA
<213> ORGANISM: Artificial sequences
<220> FEATURE:
<223> OTHER INFORMATION: Oligonucleotides

<400> SEQUENCE: 13
gcctctgggc taataggact actt                                     24
```

```
<210> SEQ ID NO 14
<211> LENGTH: 25
<212> TYPE: DNA
<213> ORGANISM: Artificial sequences
<220> FEATURE:
<223> OTHER INFORMATION: Oligonucleotides

<400> SEQUENCE: 14
ttctgaaagg ttacttcaag gacaa                                              25

<210> SEQ ID NO 15
<211> LENGTH: 17
<212> TYPE: DNA
<213> ORGANISM: Artificial sequences
<220> FEATURE:
<223> OTHER INFORMATION: Oligonucleotides

<400> SEQUENCE: 15
acctgtattc ctcgcct                                                       17

<210> SEQ ID NO 16
<211> LENGTH: 17
<212> TYPE: DNA
<213> ORGANISM: Artificial sequences
<220> FEATURE:
<223> OTHER INFORMATION: Oligonucleotides

<400> SEQUENCE: 16
acctgtattc ctcgcct                                                       17

<210> SEQ ID NO 17
<211> LENGTH: 22
<212> TYPE: DNA
<213> ORGANISM: Artificial sequences
<220> FEATURE:
<223> OTHER INFORMATION: Oligonucleotides

<400> SEQUENCE: 17
acctgtattc ctcgcctgtc ca                                                 22

<210> SEQ ID NO 18
<211> LENGTH: 14
<212> TYPE: DNA
<213> ORGANISM: Artificial sequences
<220> FEATURE:
<223> OTHER INFORMATION: Oligonucleotides

<400> SEQUENCE: 18
aagatggaac cgct                                                          14

<210> SEQ ID NO 19
<211> LENGTH: 14
<212> TYPE: DNA
<213> ORGANISM: Artificial sequences
<220> FEATURE:
<223> OTHER INFORMATION: Oligonucleotides

<400> SEQUENCE: 19
aagatggaac cgct                                                          14
```

METHOD FOR HYBRIDIZING NUCLEIC ACIDS

This application is the U.S. national phase of International Application No. PCT/IB2008/002789, filed 12 Sep. 2008, which designated the U.S., claims priority to EP Application No. 07025148.3, filed 27 Dec. 2007; and claims the benefit of U.S. Provisional No. 61/009,145, filed 27 Dec. 2007, the entire contents of each of which are hereby incorporated by reference.

The invention relates to the hybridization of nucleic acids with oligonucleotide-oligocation conjugates used for manipulating, isolating, detecting or amplifying nucleic acids and the applications thereof in the molecular biology and diagnostic field.

Nucleic acid-based technologies are widely used in cellular and molecular research and in diagnostics. The techniques rely upon the sequence recognition between a synthetic oligonucleotide and its complementary nucleic acids strand. Affinity and specificity are two major characteristics that determine efficiency of any nucleic hybridization based assay.

Different approaches have been developed to improve nucleic acid hybridization. Among them, one is to decrease the electrostatic repulsion between negatively charged acid nucleic strands. Recently, an automated solid-phase synthesis consisting in grafting cationic groups to the oligonucleotides and entirely based on the phosphoramidite chemistry used for the synthesis of oligonucleotides was disclosed in WO 2007/069092. The resulting oligonucleotide-oligocation conjugates were shown to stabilize hybridization with a short complementary sequence by decreasing interstrand phosphate repulsions (Pons et al., 2006).

Like looking for a needle in a haystack, improving the specific detection of a unique sequence in a complex nucleic acid biological sample such as a total genome is a more difficult challenge. In such a situation, one would expect that the cationic part of an oligonucleotide-oligocation conjugate sticks none specifically to phosphate groups of genomic DNA, thereby decreasing the specific recognition of the targeted sequence. This concern may become more acute when the polycation is a polyamine, as exemplified in WO 2007/069092 and (Pons et al., 2006). Indeed, polyamines such as spermine or spermidine interact naturally with genomic DNA in prokaryotic and eukaryotic cells (reviewed in Tabor and Tabor, 1984; Pegg et al., 1986). Moreover, it is established that binding affinity and sequence specificity generally negatively correlate, due to the mechanism that governs nucleic acid base-pairing interaction (Demidov and Frank-Kamenetskii, 2004). Accordingly, oligonucleotide-oligocation conjugates used to target a specific sequence in a whole genome are expected to tolerate mismatches resulting in a decrease in specificity.

The present invention discloses the unexpected finding that a specific selection of oligonucleotide-oligocation conjugates from molecules described in WO 2007/069092 demonstrates a very high affinity and surprisingly a strict specificity for their target sequence, resulting in, a general improvement of hybridization based methods. Said oligonucleotide-oligocation conjugates were particularly shown to improve Polymerase Chain Reaction.

Advantageously, said oligonucleotide-oligocation conjugates are particularly efficient compared to standard oligonucleotides as primers and probes. "Standard oligonucleotides" designates unmodified oligonucleotides that contain natural nucleobases.

An object of the invention is then to provide a method of hybridization using specific oligonucleotide-oligocation conjugates in view of targeting nucleic acids.

Another object of the invention relates to the use of the oligonucleotide-oligocation conjugates as primers or probes.

According to still another object, the invention relates to the biological applications of said conjugates.

The method for detecting, isolating, amplifying or manipulating a target nucleic acid in a sample by hybridization with an oligonucleotide-oligocation conjugate, comprises allowing said nucleic acid to react with an oligonucleotide-oligocation conjugate comprising at least $A_i$ and $B_j$ moieties linked together directly or via a linker,
wherein
$A_i$ is an i-mer oligonucleotide, with i=3 to 50, where $A_i$ is an oligomer with naturally or non naturally occurring nucleobases and/or pentafuranosyl groups and/or native phosphodiester bonds, optionally comprising a marker group $B_j$ is a j-mer organic oligocation moiety, with j=1 to 50, where B is
$HPO_3$—$R_1$—$(NH$—$R_2)_n$—$NH$—$R_3$—$O$—, where $R_1$, $R_2$ and $R_3$ are lower alkylene, identical or different, $NH$—$R_2$ moieties being identical or different when n is >1;
$HPO_3$—$R_1$—$CH(X)$—$R_3$—$O$—, where $R_1$ and $R_3$, identical or different, are lower alkylene and X is putrescine, spermidine or spermine residue.

"Lower alkylene", as used in the description and the claims, designates an optionally substituted C1-C6 linear, branched or cyclic alkylene radical.

$A_i$ is selected from the group comprising deoxyribonucleotides, ribonucleotides, and non naturally occurring nucleobases such as locked (LNA) nucleotides, PNA as well as their chemical modifications or substitutions such as phosphorothioate (also designated thiophosphate), 2'-fluoro or a 2'-O-alkyl groups.

$A_i$ may comprise a chromophore/fluorophore group and/or a quencher group, or a chemical moiety such as amino or thiol modifier, spacer group, biotin, hydrophobic chain, cholesterol derivative, antigen, protein, peptide, phosphate group or sugar.

In a first embodiment, a free —OH group is present at position 3' of $A_i$. The oligonucleotide-oligocation conjugate is thus useful as a substrate for DNA or RNA polymerases.

In this first embodiment, the oligonucleotide-oligocation conjugate is thus useful as a primer for nucleic acid synthesis.

Mixed oligonucleotide-oligocation conjugates according to said first embodiment have

HO-³'$A_i$⁵'-$B_j$-$R_4$                                    structure I or

HO-³'$A_i$⁵'-$R_5$-$B_j$-$R_4$                             structure II or

HO-³'$A_{i1}$⁵'-$B_j$-$A_{i2}$-$R_4$                        structure III wherein
$A_{i1}$ and $A_{i2}$ identical or different, are as above defined for $A_i$; $A_{i2}$ being oriented 3'-5' or 5'-3',
$R_4$ is H or a linker, a quencher, a marker such as a chromophore or fluorophore group, or a chemical moiety such as biotin, hydrophobic chain, cholesterol derivative, antigen, protein, peptide, sugar or phosphate group;
$R_5$, different from H, $A_i$ and $B_j$, is a linker between $A_i$ and $B_j$ and consists of a chemically stable or cleavable linker.

The invention thus relates to a method such as above defined, wherein a molecule of structure I, II or III is used as a primer after binding to a target nucleic acid.

Such a method advantageously comprises the steps of
incubating a primer such as above defined with the target nucleic acid molecule under conditions that allow said primer molecule to bind said target nucleic acid molecule and
extending said primer with said target nucleic acid molecule as a template.

In said embodiment, said molecules are substrates for a DNA or RNA polymerase which catalyses nucleic acid synthesis.

As shown in the examples, compared to standard unmodified oligonucleotides that contain natural nucleobases, primers corresponding to said molecules are capable to significantly improve the affinity for their target nucleic acid with unexpected high sequence specificity.

Particularly, said molecules are then powerful tools for reverse-transcription and acid nucleic amplification methods such as Polymerase Chain Reaction.

Said primers indeed enable to carry out highly efficient, specific and sensitive amplification reactions such as PCR.

Due to the outstanding affinity for their target, primers of the invention can be used at very low concentrations reduced up to 10-fold when compared to standard primers (unmodified oligonucleotides). Moreover, they perform efficiently at low salt concentration, more particularly $MgCl_2$ concentration.

The hybridization temperature can be increased by several degrees compared to standard primers. It can be modulated according to the length of the oligocation.

Therefore, it is possible to get free of constraining adjustments of hybridization temperature and salt concentration, more particularly $MgCl_2$ concentration.

Said primers are useful in applications such as multiplex PCR or high throughput PCR.

Said primers also allow improved amplifications in AT-rich regions known to be difficult to amplify by PCR.

Particularly, molecules of the invention allow short primers design, useful for specific applications such as amplification in conserved regions of genomes with high variability.

As shown in the examples, said primers are also useful in applications such as reverse-transcription as oligo(dT), hexamers or specific primers. Due to their outstanding affinity, they may be particularly valuable for detecting low-expressed genes.

Said primers may also be used for DNA sequencing.

In some cases, the use of a molecule of the present invention with a cleavable linker between the oligonucleotide and the oligocation moiety may be useful. In such methods where an electrophoretic separation of the amplification products is required, the post-amplification cleavage of the polycation prior to the separation may be valuable.

In a second embodiment, the —OH group at position 3' of $A_i$ is blocked and thus $A_i$ cannot be extended in the presence of a polymerase.

Molecules of said second group have

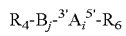  Structure IV or

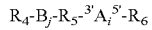  structure V or

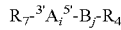  structure VI or

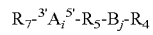  structure VII or

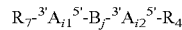  structure VIII or

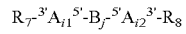  structure IX or

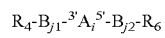  structure X wherein
$A_{i1}$ and $A_{i2}$ identical or different, are as above defined for $A_i$;
$A_{i1}$ and $B_{j2}$, identical or different, are as above defined for $B_j$;
$R_4$ and $R_6$, are identical or different, $R_4$ being as above defined and $R_6$ such as above defined for $R_4$, and
$R_7$ and $R_8$, identical or different, are different from H and are selected in the group comprising a linker, a quencher, a marker such as a chromophore or fluorophore group, or a chemical moiety such as biotin, hydrophobic chain, cholesterol derivative, antigen, protein, peptide, phosphate group or sugar.

Molecules of said second embodiment are used for detecting a target nucleic acid in an assay comprising a DNA or RNA polymerase. They are more particularly useful as probes to detect a complementary nucleic acid generated by an in vitro nucleic acid amplification process, such as PCR.

Molecules of said second embodiment are more particularly useful as probes for monitoring real-time nucleic acid amplification.

The invention relates to a method for detecting a target nucleic acid wherein a molecule of structure IV to X can be used as probe to hybridize to a target nucleic acid.

The invention thus relates to a method such as above defined for detecting a target nucleic acid, comprising the steps of
incubating said target nucleic acid with a probe such as above defined in the presence of a RNA or DNA polymerase under conditions that allow said probe to hybridize to said target nucleic acid molecule; and
detecting said hybridization.

Advantageously, said molecules are valuable hybridization probes and dual-labeled probes for real-time PCR. As shown in the examples, probes of the present invention decrease the fluorescence background, thereby improving the performance of amplicon detection.

Particularly, compared to standard probes (dual-labeled probes containing natural nucleobases), dual-labeled probes of the present invention show a greater quenching of the fluorescence emission in absence of amplification. Moreover, as shown in the examples, conjugated probes detect the target with a higher sensitivity.

The invention thus relates to a method such as above defined for distinguishing between a wild-type and a mutant target nucleic acid.

Advantageously, said molecules allow the design of shorter probes, useful in amplification processes such as PCR by facilitating the design of the primers/probe set. Short probes have a greater discrimination capability. Particularly, said molecules are then powerful tools for allelic discrimination.

As shown in the examples, compared to standard oligonucleotides, probes corresponding to molecules of the invention are particularly useful for detecting and analyzing mutations such as SNP (Single Nucleotide Polymorphism).

In another aspect, molecules of said second embodiment are advantageously used as clamps providing a method for inhibiting the amplification and/or the detection of a target nucleic acid.

In a third embodiment, molecules of the present invention are more generally used in a hybridization based assay where the target nucleic acid is not a template for a polymerase.

The invention relates to a method for nucleic acid manipulation wherein a molecule of structure I to X such as above defined is used as a substrate for one or more enzymes after binding to a target nucleic acid.

The invention relates to a method for nucleic acid manipulation wherein a molecule of structure I to X such as above defined binds to a target nucleic acid in presence of one or more enzymes under conditions that allow said enzymes to modify said target nucleic acid.

The invention relates to a method for manipulating, detecting, capturing a target nucleic acid comprising a molecule of structure I to X such as above defined to hybridize to a target nucleic acid.

The invention thus relates to a method such as above defined for detecting a target nucleic acid, comprising the steps of
incubating said target nucleic acid with a probe of the invention such as above defined under conditions that allow said probe to hybridize to said target nucleic acid molecule; and
detecting said hybridization.

Molecules of said third embodiment are more particularly useful as probes for detecting immobilized target nucleic acids such as on a solid support or on fixed tissues. Said probes are useful for In Situ Hybridization methods.

As shown in the examples, short probes of the invention can detect a target nucleic acid immobilized on a support with a high specificity under stringent conditions that are not permissive for the standard probe.

Molecules with $A_i$ containing modified nucleotides such as phosphorothioate nucleotides are particularly advantageous in view of their biological applications, since phosphorothioate oligonucleotides are not hydrolyzed in cell lysates or biological fluids.

The above defined mixed oligonucleotide-oligocation conjugates are advantageously stepwise synthesized on an oligonucleotide synthesizer, via the phosphoramidite route according to the method of said WO 2007/069092.

The activated and protected oligocations B are advantageously obtained by protecting the amino groups of a polyamine, followed by α, ω-bis hydroxylalkylation, leading to diols compatible with oligonucleotide synthesis.

Classical DMT and phosphoramidite elongation chemistry is advantageously implemented together with base-labile TFA protecting groups.

Figure 2:
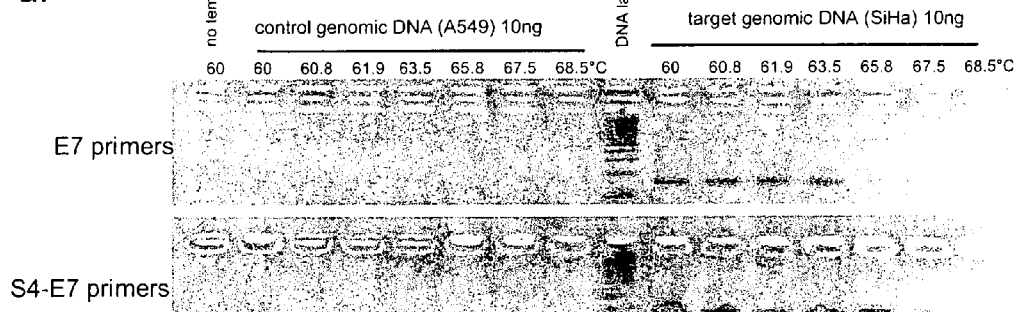
Figure 2:
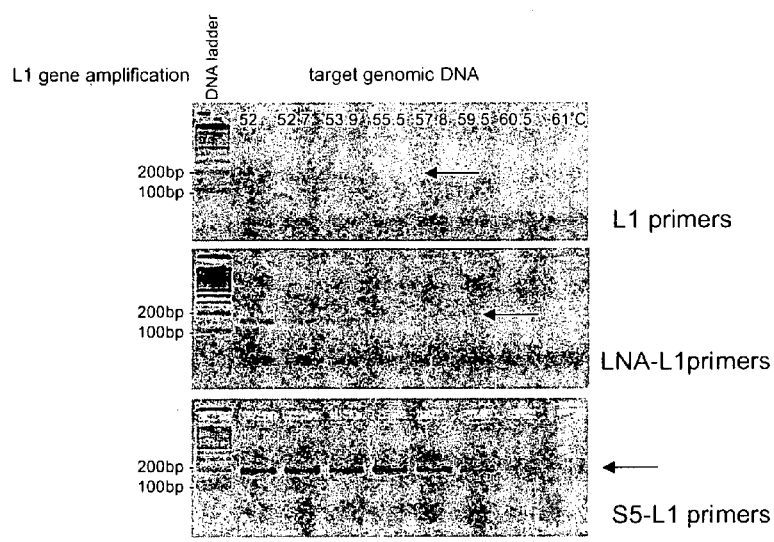
Figure 2:
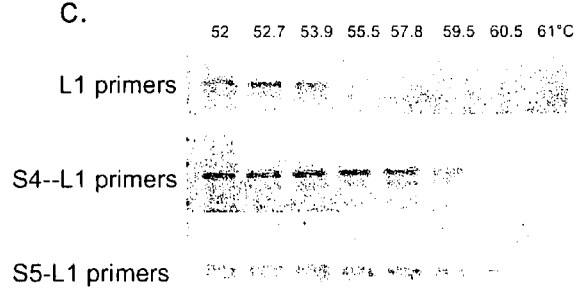
Figure 3:
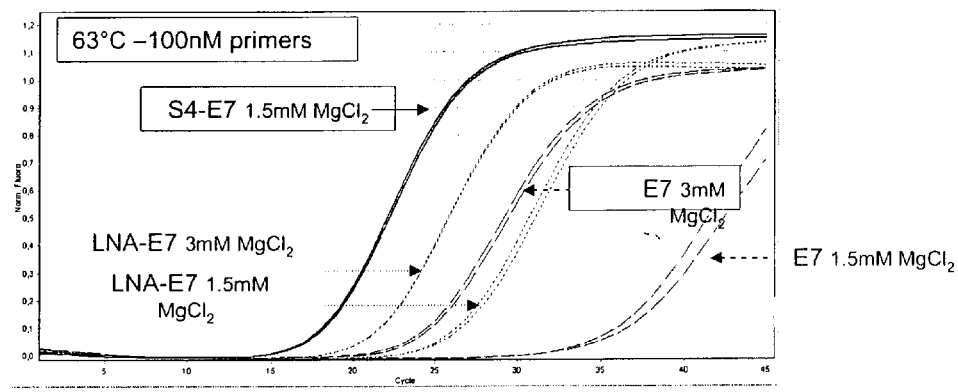
Figure 3:
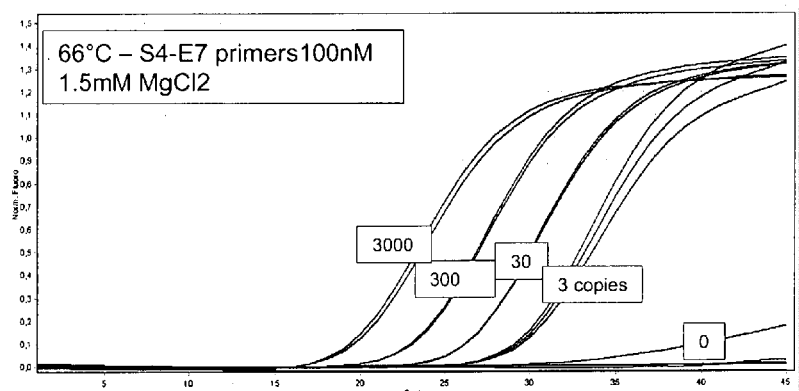
Figure 3:
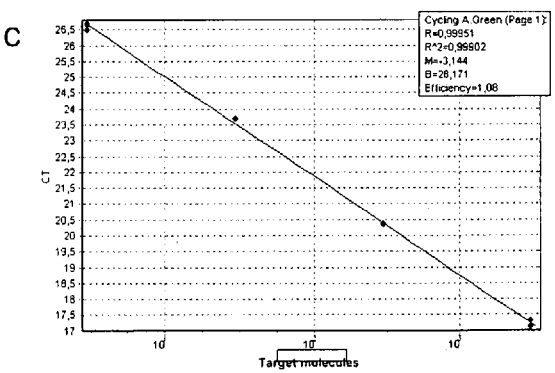
Figure 4:
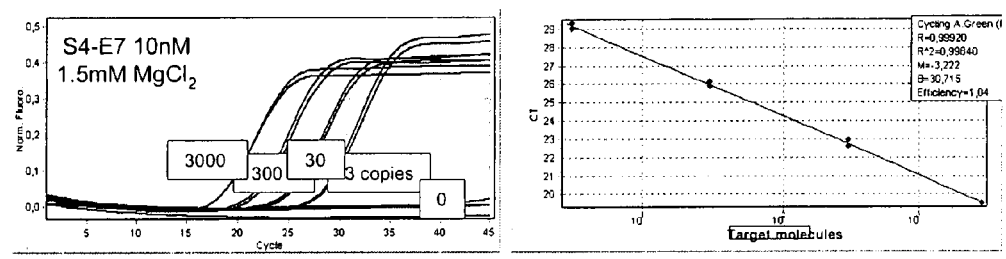
Figure 4:
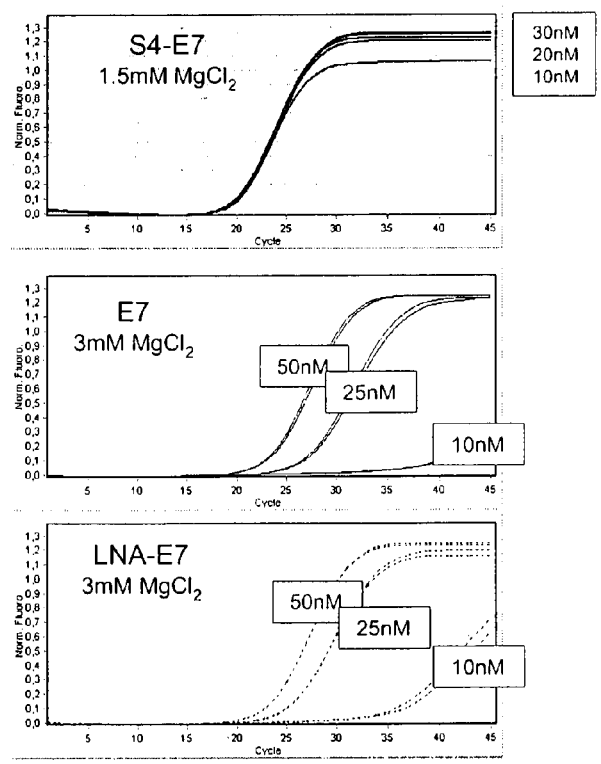
Figure 5:
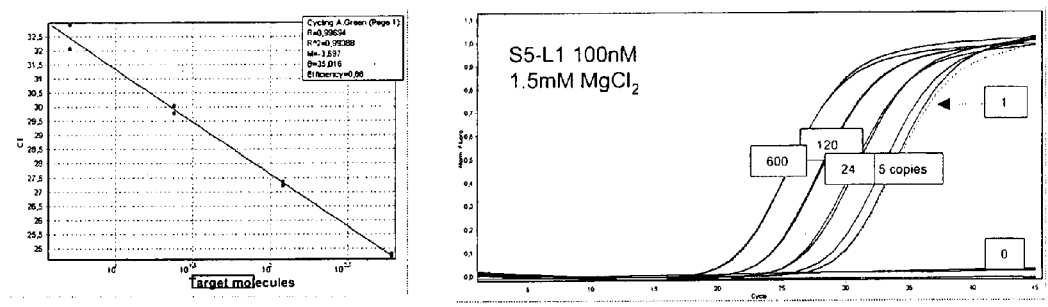
Figure 5:
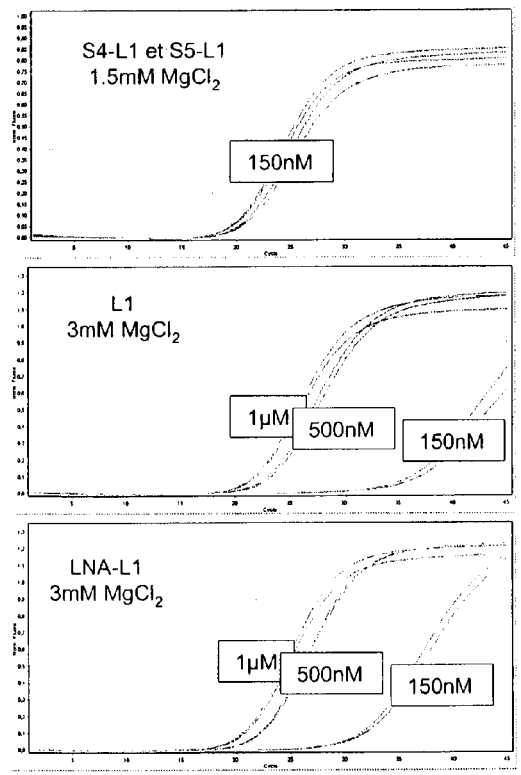
Figure 6:
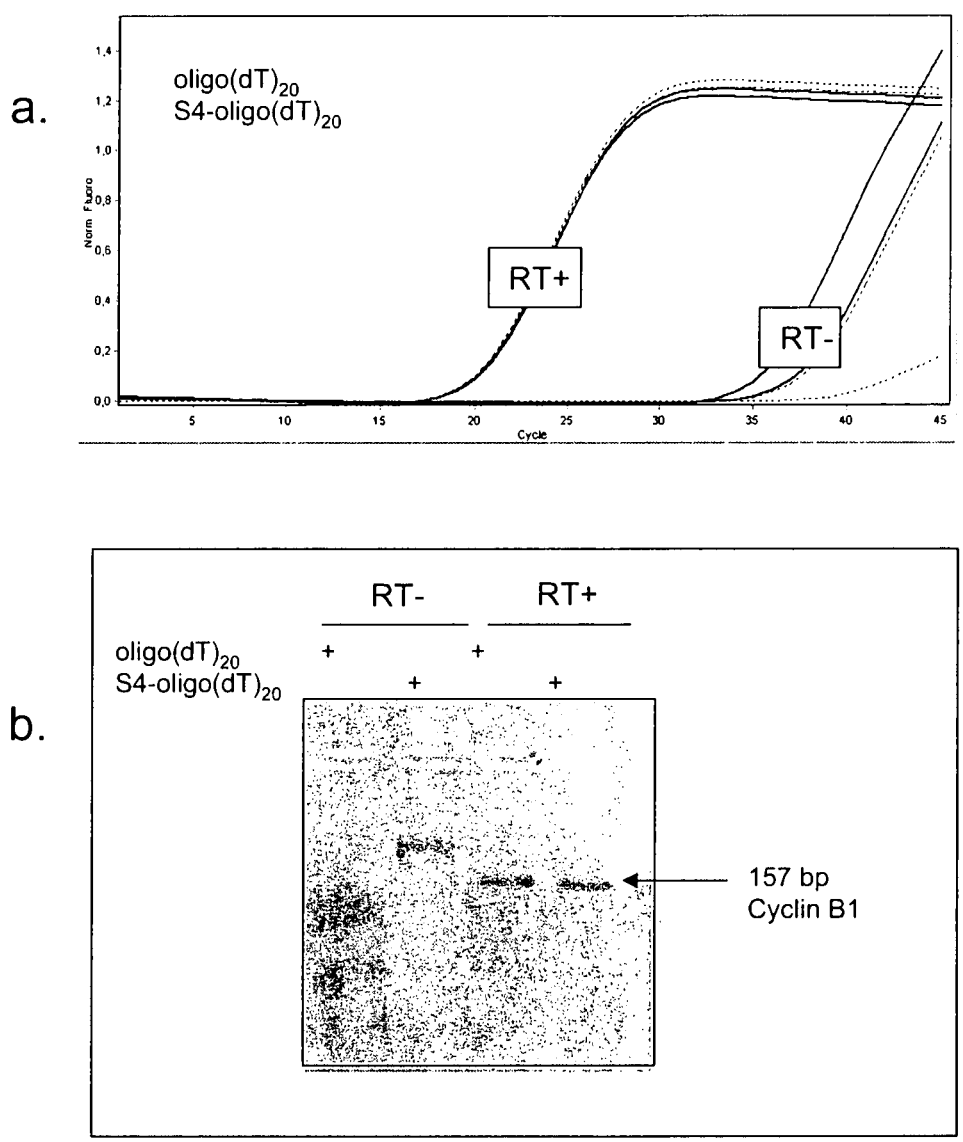
Figure 7:
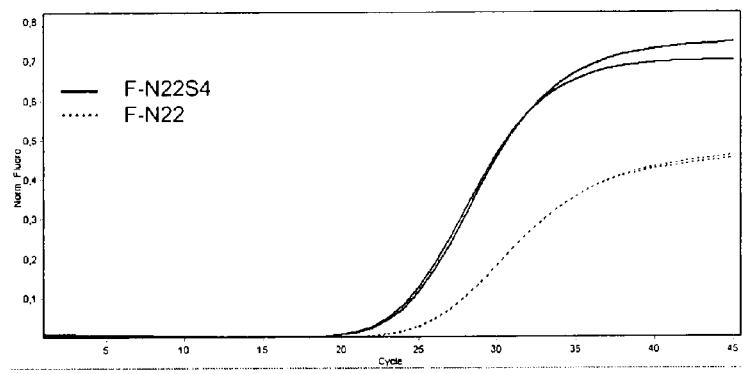
Figure 7:
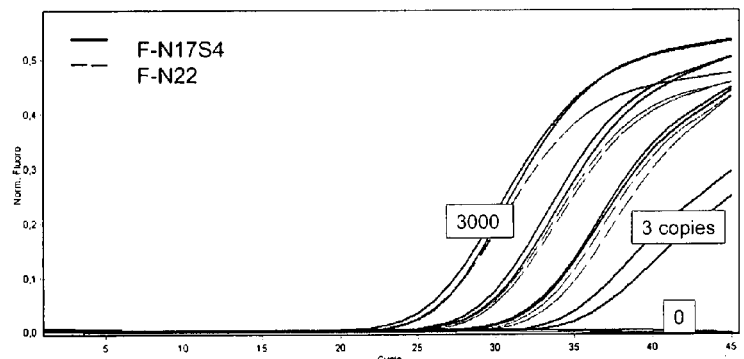
Figure 7:
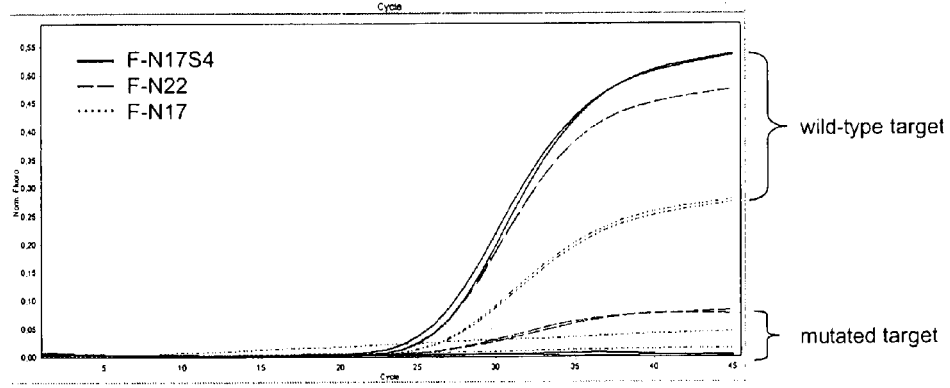
Figure 8:
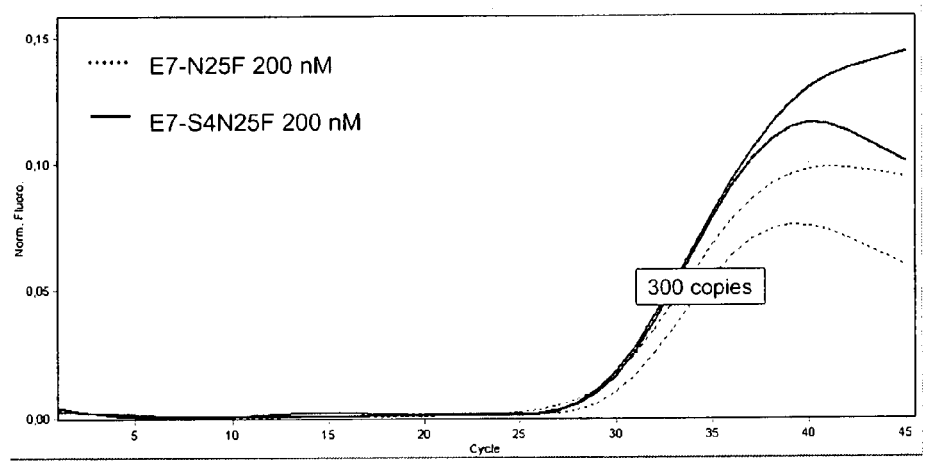
Figure 8:
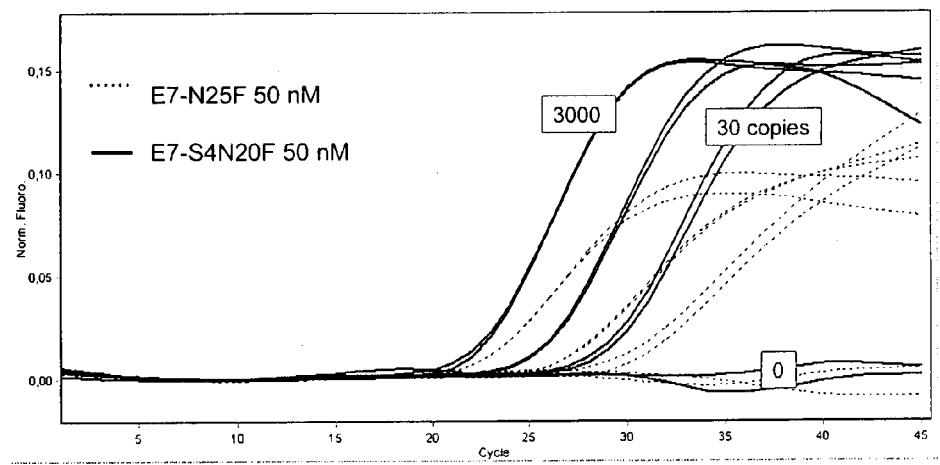
Figure 9:
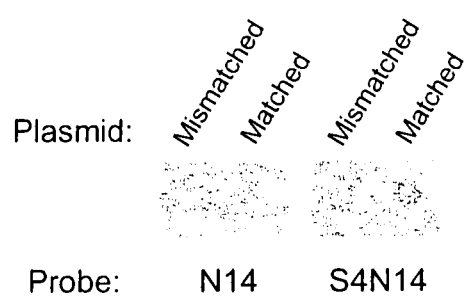

Other characteristics and advantages of the invention are given in the following examples wherein it is referred to FIGS. 1 to 9, which represent, respectively:

FIG. 1, the structure of an oligonucleotide-oligocation conjugate;

FIG. 2, results obtained with primers of the invention in conventional gradient PCR;

FIG. 3, results obtained with primers of the invention at high annealing temperature and low salt ($MgCl_2$) in real-time PCR experiments;

FIG. 4, results obtained with said primers at low concentration in real-time PCR experiments;

FIG. 5, results obtained with said primers in AT-rich context in real-time PCR experiments;

FIG. 6, results obtained in RT-qPCR on cDNA primed with a primer of the invention;

FIG. 7, fluorescence characteristics and results obtained with dual-labeled fluorogenic probes of the invention in a 5' nuclease assay;

FIG. 8, results obtained with fluorescent hybridization probes of the invention in real-time PCR;

FIG. 9, results obtained with a fluorescent probe of the invention used for detecting a target nucleic acid immobilized on a solid support.

In the following examples, "S" designates a spermine residue of structure:

$HPO_3$—$(CH_2)_4$—$NH_2^+$—$(CH_2)_3$—$NH_2^+$—$(CH_2)_4$—$NH_2^+$—$(CH_2)_3$—$NH_2^+$—$(CH_2)_4$—O— and Sn indicates the number of spermine residues with n=1 to 50.

"Nm" designates a m-mer oligonucleotide.

EXAMPLE 1

Structure of the Oligonucleotide-Oligocation Conjugate of the Invention

The synthesis is carried out according to WO 2007/069092 and the structure of the oligonucleotide-oligocation conjugate is illustrated on FIG. 1.

EXAMPLE 2

Use of Oligonucleotide-Oligocation Conjugates as PCR Primers

Two couples of oligonucleotide-oligocation primers specific to genes E7 and L1 of the human papillomavirus type 16 (HPV 16) were compared to their standard counterparts (non conjugated oligonucleotides). The molecules of the invention were also compared to Locked Nucleic Acid (LNA) modified primers.

Sequences of E7 primers are from Hesselink et al., 2005. Sequences of L1 primers are adapted from de Roda Husman et al., 1995.

E7 primer pair (46% and 48% GC) and L1 primer pair (30% and 20% GC) illustrate two different GC contents.

Genomic DNA of SiHa cells (cervical carcinoma, ATCC HTB35) containing 1 to 2 copies of integrated HPV16 was used as target genomic DNA. The genomic DNA of A549 cells (lung carcinoma, ATCC CCL185) which does not contain the virus was used as negative control.

Primers of the present invention are examples of structure I.

Sequences of the standard oligonucleotides (E7 primers)

```
Forward primer of SEQ ID N° 1 (E7F):
5'-GAG GAG GAG GAT GAA ATA GAT GGT-3'

Reverse primer of SEQ ID N° 2 (E7R):
5'-GCC CAT TAA CAG GTC TTC CAA-3'
```

Sequences of the oligonucleotide-oligocation conjugates according to the invention (S4-E7 primers)

```
Forward primer of SEQ ID N° 3 (S4-E7F):
5'-S4-GAG GAG GAT GAA ATA GAT GGT-3'

Reverse primer of SEQ ID N° 4 (S4-E7R):
5'-S4-GCC CAT TAA CAG GTC TTC CAA-3'
```

Sequences of the LNA containing oligonucleotides (LNA-E7 primers)

```
Forward primer of SEQ ID N° 5 (LNA-E7F):
5'-GaG GAq GAG GAT GAA ATA GAT GGT-3'

Reverse primer of SEQ ID N° 6 (LNA-E7R):
5'-GCc CAT tAA CAG GTC TTC CAA-3'
```

LNA nucleotides are underlined and in lower case
$S_4$=4 spermine moieties

Sequences of the standard oligonucleotides (L1 primers)

```
Forward primer of SEQ ID N° 7 (L1F):
5'-TTT GTT ACT GTT GTT GAT ACT AC-3'

Reverse primer of SEQ ID N° 8 (L1R):
5'-GAA AAA TAA ACT GTA AAT CAT ATT C-3'
```

Sequences of the primers according to the invention (Sn-L1 primers)

```
Forward primer of SEQ ID N° 9 (Sn-L1F):
5'-Sn-TTT GTT ACT GTT GTT GAT ACT AC-3'

Reverse primer of SEQ ID N° 10 (Sn-L1R):
5'-Sn-GAA AAA TAA ACT GTA AAT CAT ATT C-3'
```

Sn=n spermine moieties; n=4 and 5

Sequences of the LNA containing oligonucleotides (LNA-L1 primers)

```
Forward primer of SEQ ID N° 11 (L1F):
5'-TTt GTT aCT GTT GTT GAT ACT AC-3'

Reverse primer of SEQ ID N° 12 (L1R):
5'-GAa AAA tAA ACT GTA AAT CAT ATT C-3'
```

LNA nucleotides are underlined and in lower case

FIG. 2 depicts the use of primers of the present invention in conventional PCR. Amplification performances were evaluated at the end-point of PCR as a function of annealing temperatures using a gradient PCR procedure.

Target and control genomic DNA were amplified in a reaction volume of 25 μl. Each sample was amplified in the presence of 0.4 mM DNA, 10 mM Tris-HCl (pH9), 50 mM KCl, 1.5 mM MgCl$_2$, 0.1% Triton X-100, 200 μM dNTP (each), 0.04 U/μl of EconoTaq DNA Polymerase (Lucigen) and the following primer pairs:
  100 nM of E7 standard primers (FIG. 2a: upper panel) or S4-E7 primers (FIG. 2a: lower panel), or
  500 nM of L1 standard primers (FIG. 2b: upper panel); LNA-L1 primers (FIG. 2b: middle panel); and S5-L1 primers with 5 spermine moieties (FIG. 2b: lower panel),
  500 nM of L1 standard primers (FIG. 2c: upper part); S4-L1 primers with 4 spermine moieties (FIG. 2c: medium part); and S5-L1 primers with 5 spermine moieties (FIG. 2c: lower part).

Gradient amplifications were carried out in a iCycler thermal cycler (Biorad) as follows: initial denaturation: 3 min at 95° C., cycling: 35 (a, c) and 30 (b) cycles: 94° C. for 20 s, 60° C.-69° C. (a) for 20 s or 52° C.-61° C. (b, c) for 20 s, 72° C. for 15 s; final extension: 5 min at 72° C. Final PCR reactions were analysed on agarose gel 4%. E7 and L1 product size is 159 bp and 142 bp, respectively.

As shown on FIG. 2a, the conjugates selected according to the invention having 4 spermine residues at the 5' end, specifically amplify their target. Like the standard primers, they indeed amplify a viral sequence fragment having the expected size of 159 bp from the genomic DNA of target SiHa cells. On the contrary, no amplification is obtained from genomic DNA of A549 cells under the same conditions of amplification.

Advantageously, by using the oligonucleotide conjugates of the invention, the hybridization reaction can be carried out at a higher temperature (4 to 7° C. depending on the primer pair) (FIGS. 2a and 2b).

Advantageously, by using the oligonucleotide conjugates of the invention, the hybridization reaction can be carried out at a higher temperature than LNA containing primers (4-5° C., see FIG. 2b).

The results given in FIG. 2c show that the gain in temperature can be modulated with the number of spermines conjugated to the oligonucleotide.

The molecules of the invention were evaluated for their use as primers in real-time PCR experiments. Primer conjugates have been compared to their unmodified standard counterparts as well as to LNA-containing primers.

All reactions have been conducted in a Rotor-gene 6000 instrument (Corbett) in a final volume of 10 μl. Reactions were carried out using the Sensimix NoRef DNA kit (Quantace) at a final concentration of 0.5×.

Efficiency and sensitivity have been evaluated by amplifying serial dilutions of genomic DNA of target HPV16 positive cells (SiHa cells) spiked in 10 ng of control genomic DNA, i.e. 3000 genomes of HPV negative cells (A549 cells).

The samples were amplified under various conditions of hybridization temperature, MgCl$_2$ concentration or primer concentration, using SYBR Green I for detection.

FIG. 3: Effects of the MgCl$_2$ concentration and the annealing temperature on real-time amplification.

Reactions were performed on 10 ng of target genomic DNA and with 100 nM of each primer. Final MgCl$_2$ concentration was 1.5 mM or 3 mM, as indicated. A hot-start of 10 min at 95° C. was followed by 45 cycles of 94° C. for 20 s, 63° C. (a) or 66° C. (b) for 20 s and 72° C. for 15 s.

As shown in FIG. 3a, the molecules of the invention (S4-E7) are optimal when annealed at 63° C. in 1.5 mM MgCl$_2$. Comparatively, standard primers and LNA containing primers are inefficient as shown by the increase in cycle threshold (16 for conjugates of the invention, 33 for standard primers and 24 for LNA containing primers). Increasing the MgCl$_2$ concentration improves standard and LNA containing primers performances. It also results from said FIG. 3 that a lower annealing temperature is required with standard primers and LNA containing primers, while said S4-E7 conjugates perform efficiently at 63° C.

As shown on FIGS. 3b and 3c, at a fixed concentration of primers (100 nM) and low concentration of MgCl$_2$ (1.5 mM), up to 3 copies of the target are detectable with said S4-E7 conjugates, with a high reproducibility, specificity and efficiency at an hybridization temperature of 66° C.

Specific, efficient and sensitive amplifications are obtained with the primer conjugates of the invention, under temperature or MgCl$_2$ conditions generally suboptimal for the standard primers and LNA containing primers.

Effect of primer concentration is illustrated by FIG. 4.

FIG. 4a: 10-fold serial dilutions of target genomic DNA were amplified with 10 nM of primer conjugates of the invention in 1.5 mM MgCl$_2$.

FIG. 4b: 2 ng of target genomic DNA spiked in 10 ng of control genomic DNA were amplified using variable amount of primers: 10, 20 and 30 nM of primer conjugates of the invention (upper panel); 10, 25 and 50 nM for standard primers (middle panel) and LNA containing primers (lower panel). MgCl$_2$ concentration was 1.5 mM for conjugates of the invention and 3 mM for standard and LNA containing primers.

Amplifications were performed as follows: 95° C. for 10 min followed by 45 cycles of 95° C. for 10 s, 60° C. for 1 min.

FIG. 4a shows that 10 nM of primer molecules of the present invention drive efficient and sensitive amplifications in two-step PCR reactions. 3 copies of the target are indeed quantitatively detected. As shown on FIG. 4b, reduction in primer concentration does not induce an increase in the Ct value. Only the final amount of amplicon at the reaction end-point is decreased. Comparatively, 50 nM of standard oligonucleotides or LNA-containing primers in 3 mM of MgCl$_2$ are not sufficient to amplify the target in an optimal way as the conjugated primers do.

Advantageously, primer conjugates of the invention show a greater affinity to their target allowing their use at low MgCl$_2$ concentration compared to standard oligonucleotides and LNA containing primers. Said molecules allow a reduction of the primer concentration up to 10-fold compared to standard oligonucleotides and LNA containing primers, without loss of sensitivity, efficiency, specificity nor reproducibility.

As shown in FIG. 5, primer molecules of the invention improve PCR in AT-rich sequences. Advantageously, said molecules allow to perform efficient reaction in standardized conditions (1.5 mM MgCl$_2$, annealing at 60° C.).

In FIG. 5a, 5-fold serial dilutions of target genomic DNA were amplified with 100 nM of conjugates of the invention. Final MgCl$_2$ concentration was 1.5 mM. Reactions were incubated 95° C. for 10 min followed by 45 cycles of 94° C. for 20 s, 60° C. for 20 s and 72° C. for 15 s. Under these conditions, conjugates of the invention drive efficient (see the standard curve (E=0.89; R$^2$=0.992)) and sensitive amplifications as shown by the detection of 1 copy of target.

Comparatively (FIG. 5b), 600 copies of targets are inefficiently amplified by standard and LNA containing primers. Conditions were the following: 2 ng of target genomic DNA (representing 600 copies of target) spiked in 10 ng of control genomic DNA have been amplified using a two-step amplification protocol (95° C. for 10 min followed by 45 cycles of 95° C. for 10 s, 60° C. for 1 min) with 150 nM of conjugates of the invention (with 4 or 5 spermines) (upper panel); 150 nM, 500 nM and 1 µM for standard primers (middle panel) and LNA containing primers (lower panel). MgCl$_2$ concentration was 1.5 mM for conjugates of the invention and 3 mM for standard and LNA containing primers.

EXAMPLE 3

Use of Oligonucleotide-Oligocation Conjugates as Primer for Reverse-Transcription The molecules of the invention were evaluated for their use as primer for reverse-transcription. cDNA from total RNA was synthesized using either a polydeoxyribothymidine containing 20 residues conjugated with 4 spermine moieties (S4-oligo(dT)$_{20}$) or its unconjugated counterpart (oligo(dT)$_{20}$). Subsequent RT-qPCR reactions for amplification of the cyclin B1 transcript were performed to compare the reverse-transcription efficiency.

Sequences of the primers

```
oligo(dT)20 of SEQ ID N° 13:
5'-TTTTTTTTTTTTTTTTTTTT-3'

S4-oligo(dT)20 of SEQ ID N° 14:
5'-S4- TTTTTTTTTTTTTTTTTTTT-3'
S4 = 4 spermine moieties Cyclin B1 forward primer of SEQ ID N° 15:
5'-TCTGGATAATGGTGAATGGACA-3'

Cyclin B1 reverse primer of SEQ ID N° 16:
5'-CGATGTGGCATACTTGTTCTTG-3'
```

Total RNA from cells HCT 116 (from ATCC CCL-247) was extracted using the SV Total RNA Isolation kit (Promega). One µg of total RNA was reverse-transcribed using the SuperScript III First-Strand Synthesis System for RT-PCR (Invitrogen) as described by the supplier. Reactions (RT+) were either primed using 50 µM of the molecule of the invention (S4-oligo(dT)$_{20}$) or its unconjugated counterpart (oligo(dT)$_{20}$). Reactions without reverse-transcriptase (RT−) were performed as control.

FIG. 6 shows RT-qPCR amplifications of the Cyclin B1 transcript carried out using cDNA synthesis reactions (RT+ and RT−) corresponding to 5 ng of total RNA. PCR reactions have been conducted in a Rotor-gene 6000 instrument (Corbett) in a final volume of 10 µl. Final reaction mixtures contained 2.5 µSensimix NoRef PCR kit (Quantace), SYBR Green 0.5×, 100 nM each Cyclin B1 specific primer and 3 mM MgCl$_2$.

Reactions were incubated at 95° C. for 10 min followed by 45 cycles of 95° C. for 10 s, 60° C. for 1 min.

PCR products were analyzed by gel electrophoresis on 4% agarose gel (FIG. 6b)

FIG. 6a shows identical cyclin B1 amplification curves from cDNA samples primed with the molecule of present invention or its standard counterpart. Identical PCR products at the expected size (157 bp) have been synthesized (FIG. 6b). Late off-target products occurred in absence of the reverse-transcriptase in all samples.

The conjugated oligo(dT)-OH molecule of the present invention enables efficient cDNA synthesis when used as a primer for reverse-transcription.

EXAMPLE 4

Use of Oligonucleotide-Oligocation Conjugates as Dual-Labeled PCR Probe in Real-Time PCR Dual-labeled probes are the most widely used probes for monitoring the amplification in real-time PCR. Also called TaqMan™ probes, they consist of an oligonucleotide sequence hybridizing internally to the amplicon with a fluorophore attached at the 5' end and a quencher at the 3' end (Livak et al., 1995). If both labels are close enough in solution, the energy emitted by the excited fluorophore is absorbed by the quencher through the process of FRET (fluorescence energy transfer), leading to a low fluorescence signal. During the PCR reaction based on the 5' nuclease method (Holland et al., 1991), the probe binds to the amplicon at each annealing step. When one of the primers is extended by the Taq DNA Polymerase, the probe is displaced from the template strand and hydrolyzed by the polymerase 5'-3' exonuclease activity. The cleavage leads to the release of the fluorescent reporter and causes the increase in fluorescence intensity proportional to the quantity of generated PCR product.

The oligonucleotide-oligocation conjugates of the invention were evaluated for their use as real-time PCR detection probes in a 5' nuclease assay designed to amplify the human Factor V gene. Leiden G1691A mutation in the human Factor V gene was used as a model for evaluating the capability of said probes for SNP (single nucleotide polymorphism) genotyping.

Probes and primers sequences were adapted from Luderer et al., 2004.

Two oligonucleotides containing 17 and 22 nucleotides residues were conjugated with 4 spermine moities at their 3' end. Said conjugates were 5' labeled with a 6 carboxyfluorescein (6-FAM, Sigma) and with a Black Hole Quencher™ (BHQ-1™, Glen Research) linked to the oligocation. These dual-labeled fluorogenic probe of the invention have been compared to their non oligocation-conjugated counterparts All probes were designed to detect the wild-type allele. Factor V wild-type and Leiden DNA were extracted from cell lines A549 (ATCC CCL-185) and GM14899 (Coriell Institute), respectively.

Dual-labeled probes of the present invention are examples of structure IV.

Sequences of the primers

```
Forward primer of SEQ ID N° 15:
5'-GCC TCT GGG CTA ATA GGA CTA CTT-3'

Reverse primer of SEQ ID N° 16:
5'-TT CTG AAA GGT TAC TTC AAG GAC AA-3'
```

Sequences of the probes
Sequence of the probe according to the invention:

```
SEQ ID N° 15 (F-N17S4):
5' 6-FAM- ACC TGT ATT CCT CGC CT -S4 BHQ-1
S4 = 4 spermine moieties
```

Sequence of the standard probes

```
SEQ ID N° 17 (F-N17):
5' 6-FAM- ACC TGT ATT CCT CGC CT -BHQ-1

SEQ ID N° 18 (F-N22):
5' 6-FAM- ACC TGT ATT CCT CGC CTG TCC A-BHQ-1
```

The SNP site is underlined.

PCR reactions have been conducted in a Rotor-gene 6000 instrument (Corbett) in a final volume of 10 µl. 10 ng of wild-type genomic DNA (b), 10-fold serial dilutions of wild-type genomic DNA spiked in 10 ng of control DNA (c) and 10 ng of wild-type or mutant genomic DNA (d) were used as a template. Final reaction mixtures contained 2.5 µl Sensimix NoRef PCR kit (Quantace), 200 nM each primer and 200 nM probe. Final MgCl$_2$ concentration was 3 mM. Salmon sperm DNA was used as a negative control (non target DNA).

The raw background fluorescence measured at the beginning of the PCR reaction by the instrument is an indication of the self-quenching efficiency of the dual-labeled probe. As shown in FIG. 7a, the conjugated probe of the invention (F-N22S4) exhibits a better fluorescence quenching than its standard counterpart (F-N22) (background fluorescence values 4.8 versus 24 units). Quenching is dependent on the physical proximity of the two dyes. By folding on the oligonucleotide due to electrostatic interactions, the polycation brings into proximity the terminally attached fluorophore/quencher pair. Molecules of the present invention are valuable dual-labeled probes with improved quenching characteristics FIG. 7b shows the compared performances of the probe according to the invention and its standard counterpart in 5' nuclease assay. The conjugated probe exhibits a higher signal-to noise ratio leading to earlier detection (2.5 cycles) and greater end-point fluorescence.

Thus, probes according to the invention exhibit a higher sensitivity for detecting their targets.

A short conjugated probe (17-mer, F-N$_{17}$) was then compared to a long standard probe (22-mer, F-N$_{22}$). As shown in FIG. 7c, the short probe of the invention (F-N$_{17}$S$_4$) detects the wild-type amplicon with the same efficiency and sensitivity as the long standard probe (F-N$_{22}$) does. Indeed, cycle thresholds and final fluorescence values are comparable. Under the same conditions, the short standard probe (F-N$_{17}$) performs poorly (FIG. 7d).

FIG. 7d addresses the question of allelic discrimination. In samples containing the Factor V Leiden DNA as a template, the mutated amplicon is still detected with the long wild-type standard probe, while no signal is observed with conjugated and standard short probes.

Thus, short probes according to the invention exhibit equal performance as longer conventional standard probes. Moreover, they have a greater discrimination capability.

EXAMPLE 5

Use of Oligonucleotide-Oligocation Conjugates as Fluorescent Hybridization Probe in Real-Time PCR The molecules of the invention were evaluated for their use as adjacent fluorescent probes in real-time PCR (Bernard et al., 1998). That mode of detection relies upon the hybridization of two probes adjacent one to the other on the amplicon. One probe has a 3' donor label, while the other has a 5' acceptor label. When both probes are bound to the specific amplicon, the excited 3' donor label transfers its energy to the acceptor label by the FRET mechanism which in turn emits fluorescence. The increase in donor emitted fluorescence is proportional to the increase in PCR product.

Two adjacent probes were designed to bind to the previously described human papillomavirus type 16 (HPV16) E7 amplicon during the annealing step of qPCR. The donor probe was labeled at the 3' end with a 6-FAM and the acceptor probe was labeled at the 5' end with the ROX dye (carboxy-x-Rhodamine).

The standard donor probe was compared to molecules of the present invention.

The donor probe is an example of structure VII.

300 copies (a) or serial dilutions (3000 to 30 copies) (b) of target genomic DNA (from SiHa cells) spiked in 10 ng of control genomic DNA (from A549 cells) were amplified in a Rotor-gene 6000 instrument (Corbett) in a final volume of 10 µl. Final reaction mixtures contained 2.5 µl Sensimix NoRef PCR kit (Quantace), 3 mM MgCl$_2$, 200 nM forward primer, 300 nM reverse primer, 200 nM probe E7-ROX probe (Eurogentec). Probes E7-N25F, E7-S4N25F and E7-S4N20F were 200 nM (a) and 50 nM (b).

Reactions were incubated at 95° C. for 10 min followed by 45 cycles of 95° C. for 5 s, 55° C. for 10 s, 72° C. for 10 s.

As shown in FIG. 8a, the conjugated probe enables the efficient detection of the amplicon.

Because of the spectral overlap of both labels, a high background signal is observed in absence of amplicon. Due to their high affinity, oligonucleotide-oligocation conjugates are expected to reduce the fluorescence background level by driving efficient detection at low concentration. Moreover, oligonucleotide-oligocation conjugates are expected to allow the design of efficient short probes leading to an improvement in mismatch discrimination. As depicted in FIG. 8b, a shorter probe of the present invention (E7-$S_4N_{20}$F) does indeed show better performances at low concentration than the standard probe (E7-$N_{25}$F).

Molecules of the present invention are valuable hybridization probes for real-time PCR.

Sequences of the E7 primers

```
Forward primer of SEQ ID N° 1 (E7F):
5'-GAG GAG GAG GAT GAA ATA GAT GGT-3'

Reserve primer of SEQ ID N° 2 (E7R):
5'-GCC CAT TAA CAG GTC TTC CAA-3'
```

Sequences of the probes

```
SEQ ID N° 19 (E7-ROX):
5'-ROX-TGCGTACAAAGCACACACGTAGACAT 3'

SEQ ID N° 20 (E7N25F):
5'-GCAAGTGTGACTCTACGCTTCGGTT-6-FAM 3'

SEQ ID N° 21 (E7N25F):
5'-S4-GCAAGTGTGACTCTACGCTTCGGTT-6-FAM 3'

SEQ ID N° 22 (E7S4N20F):
5'-S4-TGTGACTCTACGCTTCGGTT-6-FAM 3'
S4 = 4 spermine residues
```

EXAMPLE 6

Use of an Oligonucleotide-Oligocation Conjugate as a Fluorescent Probes for Detecting a Target Nucleic Acid Immobilized on a Solid Support The molecules of the invention were evaluated for their use as hybridization probes for detecting and/or genotyping immobilized target nucleic acids.

FIG. 9 shows results of a dot-blot DNA hybridization experiment. The target nucleic acids were pGL2 and pGL3 Luciferase Reporter vectors (Promega). A short probe (14-mer) was designed for perfectly matching to the pGL3 vector. By hybridizing to pGL2, said sequence forms a mismatch. The probe of the present invention was compared with its standard counterpart. Both probes were 5' labeled with a fluorescein.

One µg of pGL2 and pGL3 vectors were immobilized on a nylon membrane positively charged (Roche) by backing at 80° C. for 60 min and denatured by incubating the membrane in NaOH 0.4 M for 5 min. Membranes were then washed briefly in 2×SSC (Sodium Salt Citrate buffer) and air dried. Prehybridization step was performed in 5×SSC, 5×Denhardt's solution for 60 min at 55° C. Membranes were incubated for 120 min at 55° C. with 10 nM probe in 1×SSC. After 3 washes in 1×SSC at 55° C. for 5 min, membranes were scanned on a Typhoon imaging system (Amersham Bioscience).

As shown in FIG. 9, the probe of the invention enables the detection of the target nucleic acid under stringent conditions (55° C. and low salt), while the standard probe does not. No signal is detected on the mismatched target, showing the high specificity of the probe of the invention.

Sequences of the probes

```
SEQ ID N° 23 (N14):
5'-Fluorescein-AAG ATG GAA CCG CT-3'

SEQ ID N° 25 (S4N14):
5'-Fluorescein-S4-AAG ATG GAA CCG CT-3'
S4 = 4 spermine residues
```

The mismatched site is underlined.

REFERENCES

Bernard P S, Ajioka R S, Kushner J P, Wittwer C T. Homogeneous multiplex genotyping of hemochromatosis mutations with fluorescent hybridization probes. Am J Pathol. 1998 October; 153(4):1055-61.

Demidov V V, Frank-Kamenetskii M D. Two sides of the coin: affinity and specificity of nucleic acid interactions. Trends Biochem Sci. 2004 February; 29(2):62-71. Review de Roda Husman A M, Walboomers J M, van den Brule A J, Meijer C J, Snijders P J. The use of general primers GP5 and GP6 elongated at their 3' ends with adjacent highly conserved sequences improves human papillomavirus detection by PCR. J Gen Virol. 1995 April; 76 (Pt 4):1057-62.

Hesselink A T, van den Brule A J, Groothuismink Z M, Molano M, Berkhof J, Meijer C J, Snijders P J. Comparison of three different PCR methods for quantifying human papillomavirus type 16 DNA in cervical scrape specimens. J Clin Microbiol. 2005 September; 43(9):4868-71.

Holland P M, Abramson R D, Watson R, Gelfand D H. Detection of specific polymerase chain reaction product by utilizing the 5'-3' exonuclease activity of *Thermus aquaticus* DNA polymerase. Proc Natl Acad Sci USA. 1991 Aug. 15; 88(16):7276-80.

Livak K J, Flood S J, Marmaro J, Giusti W, Deetz K. Oligonucleotides with fluorescent dyes at opposite ends provide a quenched probe system useful for detecting PCR product and nucleic acid hybridization. PCR Methods Appl. 1995 June; 4(6):357-62.

Luderer R, Verheul A, Kortlandt W. Rapid detection of the factor V Leiden mutation by real-time PCR with TaqMan minor groove binder probes. Clin Chem. 2004 April; 50(4): 787-8.

Pegg A E. Recent advances in the biochemistry of polyamines in eukaryotes. Biochem J. 1986 Mar. 1; 234(2):249-62. Review.

Pons B, Kotera M, Zuber G, Behr J P. Online synthesis of diblock cationic oligonucleotides for enhanced hybridization to their complementary sequence. Chembiochem. 2006 August; 7(8):1173-6.

Tabor C W, Tabor H. Polyamines. Annu Rev Biochem. 1984; 53:749-90. Review.

The invention claimed is:

1. A method for detecting or amplifying a target nucleic acid in a sample of genomic DNA or of total RNA, comprising at least an oligonucleotide-oligocation conjugate $A_i$-$B_j$ and comprising the steps of:
   extending an oligonucleotide-oligocation conjugate $A_i$-$B_j$ of structure I to III with said target nucleic acid in a sample of genomic DNA as a template;
   detecting said target nucleic acid in said sample of genomic DNA with an oligonucleotide-oligocation conjugate $A_i$-$B_j$ of structure I to X; or
   reverse transcribing said target nucleic acid of a sample of total RNA with an oligonucleotide-oligocation conjugate $A_i$-$B_j$ of structure I to III;
   wherein in said conjugate $A_i$-$B_j$
   $A_i$ is an i-mer oligonucleotide with i=3 to 50, where $A_i$ is an oligomer with naturally or non naturally occurring nucleobases and/or pentafuranosyl groups and/or native phosphodiester bonds,
   $B_j$, moiety is attached to $A_i$ moiety or to linker to $A_i$ via a phosphodiester link,
   $B_j$, being a j-mer organic oligocation moiety, with j=1 to 50, where B is:
   —$HPO_3$—$R_1$—(NH—$R_2$)$_n$—NH—$R_3$—O—, where $R_1$, $R_2$ and $R_3$ identical or different, are a C1-C6 alkylene radical, the NH—$R_2$ moieties being identical or different when n is >1;
   —$HPO_3$—$R_1$—CH(X)—$R_3$—O— where $R_1$ and $R_3$, identical or different, are a C1-C6 alkylene radical and X is putrescine, spermidine or a spermine residue, said structures I to X being as follows:

HO—³'$A_i$⁵'-$B_j$-$R_4$     structure I

HO—³'$A_i$⁵'-$R_5$—$B_j$-$R_4$     structure II

HO—³'$A_{i1}$⁵'—$B_j$-$A_{i2}$-$R_4$     structure III $R_4$—$B_j$-³'$A_i$⁵'—$R_6$     structure IV $R_4$—$B_j$-$R_5$³'$A_i$⁵'-$R_6$     structure V $R_7$-³'$A_i$⁵'-$B_j$—$R_4$     structure VI $R_7$-³'$A_i$⁵'-$R_5$—$B_j$—$R_4$     structure VII $R_7$-³'$A_{i1}$⁵'-$B_j$-³'$A_{i2}$⁵'-$R_4$     structure VIII $R_7$-³'$A_{i1}$⁵'-$B_j$-⁵'$A_{i2}$³'-$R_8$     structure IX $R_4$—$B_{j1}$-³'$A_i$⁵'-$B_{j2}$-$R_6$     structure X wherein
   $A_{i1}$ and $A_{i2}$, identical or different are i-mer oligonucleotides with i=3 to 50, where $A_{i1}$ and $A_{i2}$ are oligomers with naturally or non naturally occurring nucleobases and/or pentafuranosyl groups and/or native phosphodiester bonds;
   $R_4$ and $R_6$, identical or different, are H or a linker, a quencher, a marker, a chromophore group, a fluorophore group, a chemical moiety, a biotin, a hydrophobic chain, a cholesterol derivative, an antigen, a protein, a peptide, a sugar group and a phosphate group;
   $R_5$, different from H, $A_i$ and $B_j$, is a chemically stable or cleavable linker between $A_i$ and $B_j$;
   $R_7$ and $R_8$, identical or different, are different from H and are selected in the group comprising a linker, a quencher, a marker, a chromophore group fluorophore group, a chemical moiety, a biotin, a hydrophobic chain, a cholesterol derivative, an antigen, a protein, a peptide, a phosphate group and a sugar group.

2. The method of claim 1, wherein said oligonucleotide-oligocation conjugate of structures I-III are used as primers for DNA or RNA polymerase.

3. The method of claim 1, allowing nucleic acid amplification using at least one oligonucleotide-olgocation conjugate of structure I, II or III.

4. The method of claim 1, wherein an oligonucleotide-oligocation conjugate $A_i$-$B_3$ of structure IV to X is used as a probe to detect said target nucleic acid.

5. The method of claim 4, wherein said oligonucleotide-oligocation is used as a probe in PCR or Real Time-PCR.

6. The method of claim 5, wherein said oligonucleotide-oligocation probe is a dual labeled probe.

7. The method of claim 1, wherein at least one of structures IV to X is used as a clamp for inhibiting the detection or amplification of a target nucleic acid.

8. The method of claim 1, wherein at least one oligonucleotide-oligocation conjugate of structure I to X is used for distinguishing between a wild-type and a mutant target nucleic acid.

9. The method of claim 1, wherein at least one oligonucleotide-oligocation conjugate of structure I to X is used in a multiplex assay.

10. The method of claim 1, further comprising purifying, capturing and modifying said target nucleic acid, using at least one oligonucleotide-oligocation of structure I to X.

11. The method of claim 1, wherein $A_i$ is selected from the group comprising deoxyribonucleotides, ribonucleotides and non naturally occurring nucleobases.

12. The method of claim 11, wherein said non naturally occurring nucleobases are locked (LNA) nucleotides, PNA, phosophorothioate modifications or substitutions or 2'-fluoro or 2'-O-alkyl groups modifications or substitutions.

* * * * *

UNITED STATES PATENT AND TRADEMARK OFFICE
CERTIFICATE OF CORRECTION

PATENT NO. : 8,465,920 B2
APPLICATION NO. : 12/735261
DATED : June 18, 2013
INVENTOR(S) : Lenne et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 298 days.

Signed and Sealed this
Eighth Day of September, 2015

Michelle K. Lee
*Director of the United States Patent and Trademark Office*